(12) United States Patent
Casset

(10) Patent No.: US 7,072,716 B2
(45) Date of Patent: Jul. 4, 2006

(54) APPARATUS FOR COMPENSATING THE AMPLIFIER POTENTIAL OF THE CIRCUITS FOR SENSING CARDIAC ACTIVITY IN AN ACTIVE IMPLANTABLE MEDICAL DEVICE

(75) Inventor: Cyrille Casset, Paris (FR)

(73) Assignee: Ela Medical S.A., Montrouge (FR)

( * ) Notice: Subject to any disclaimer, the term of this patent is extended or adjusted under 35 U.S.C. 154(b) by 751 days.

(21) Appl. No.: 10/193,658

(22) Filed: Jul. 10, 2002

(65) Prior Publication Data
US 2003/0032990 A1 Feb. 13, 2003

(30) Foreign Application Priority Data
Jul. 11, 2001 (FR) .................................. 01 09183

(51) Int. Cl.
*A61N 1/18* (2006.01)
(52) U.S. Cl. ........................................................ 607/27
(58) Field of Classification Search .................. 607/11, 607/27–28
See application file for complete search history.

(56) References Cited
U.S. PATENT DOCUMENTS

| 4,674,509 A | 6/1987 | DeCote, Jr. |
| 5,350,410 A | 9/1994 | Kleks et al. |
| 6,144,881 A | 11/2000 | Hemming et al. |

FOREIGN PATENT DOCUMENTS

| WO | WO 98/22183 | 5/1998 |

*Primary Examiner*—Mark Bockelman
(74) *Attorney, Agent, or Firm*—Orrick Herrington & Sutcliffe LLP

(57) ABSTRACT

Apparatus and technique for compensating the potential detected by amplifier circuits for sensing cardiac activity in an active implantable medical device, such as in a pacemaker, defibrillator, cardioverter and multisite device. This device includes circuits for delivering to a cardiac cavity stimulation pulses of predetermined voltage levels and pulse widths, and circuits for sensing cardiac activity comprising an amplifier of signals sensed by an intracardiac electrode, delivering at its output a value of measured potential (Pmeasured) consecutive with the application of a stimulation pulse (I). The device includes circuits for determining a response potential specific to that amplifier, independently of the presence or absence of a myocardial depolarization. Advantageously, the device extracts from the value of measured potential (Pmeasured) consecutive to the delivery of the stimulation pulse (I), the value of the specific response potential (Pampli) from the amplifier corresponding to the pulse width (Ls) and the voltage level (Vs) of the aforementioned stimulation pulse. Knowing the specific response potential allows the device to identify more reliably when the measured potential (Pmeasure) corresponds to a myocardial depolarization (Pstim).

3 Claims, 1 Drawing Sheet

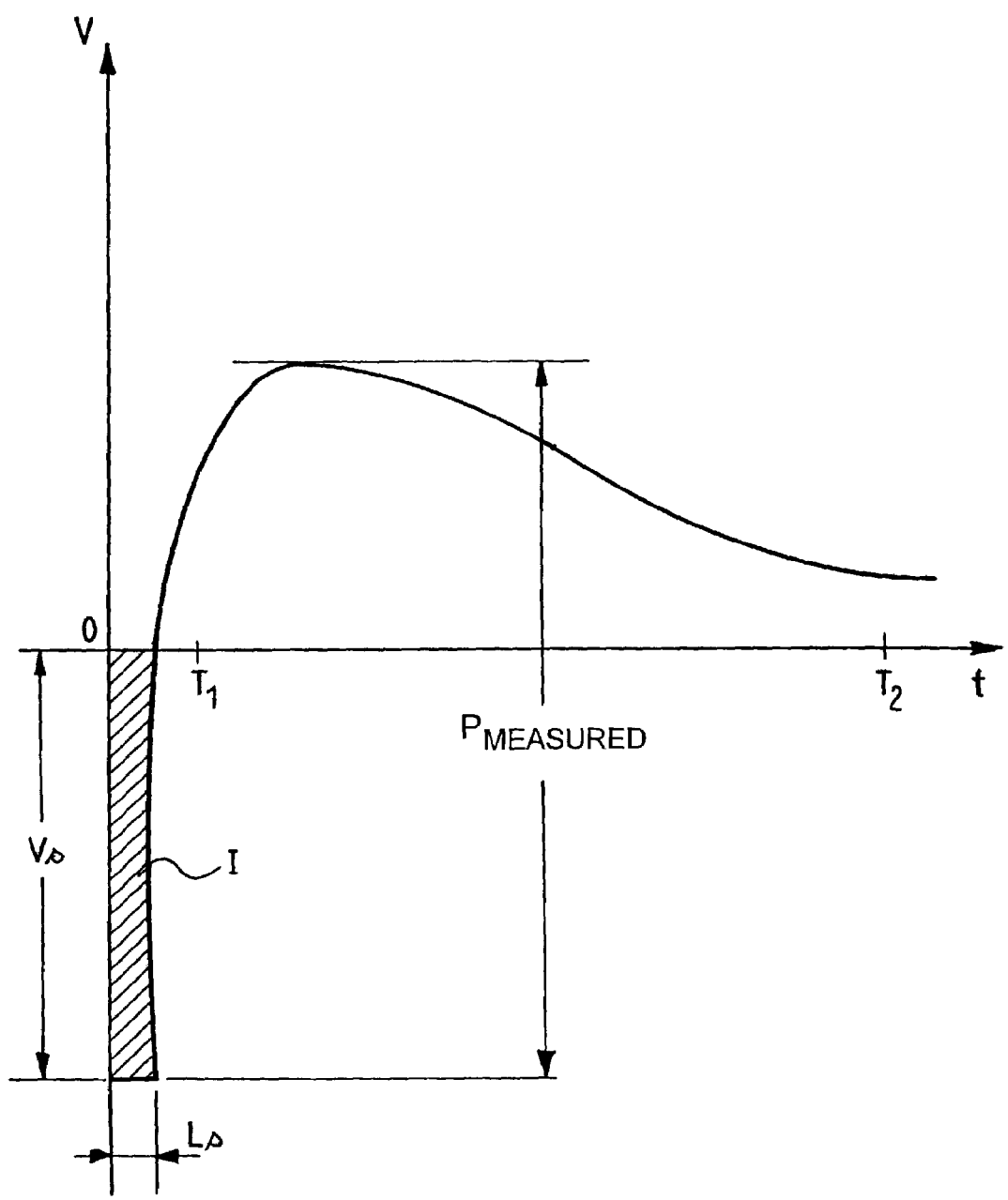
FIG_1

APPARATUS FOR COMPENSATING THE AMPLIFIER POTENTIAL OF THE CIRCUITS FOR SENSING CARDIAC ACTIVITY IN AN ACTIVE IMPLANTABLE MEDICAL DEVICE

FIELD OF THE INVENTION

The present invention is directed to "active implantable medical devices" as such devices are defined by the Jun. 20, 1990 directive 90/385/CEE of the Council of the European Communities, more particularly to pacemaker, defibrillator and/or cardiovertor devices that are able to deliver to the heart pulses of low energy for the treatment of the disorders of the heart rate.

BACKGROUND OF THE INVENTION

The active implantable medical devices for use with the present invention include those devices having circuits for detecting the cardiac activity, i.e. detecting (or sensing) the spontaneous depolarization of the myocardium, as well as circuits for stimulating the myocardium, which circuits are in themselves well-known and of different specific constructions.

It is important to be able to sense the signal resulting from the myocardial depolarization as soon as possible after the stimulation, in order to detect as accurately and quickly as possible a depolarization wave revealing an activity of the myocardial cells. This makes it possible to carry out, for example, very precise algorithms for the control of the heartbeat rate to enable or obtain a more physiological behavior of the prosthesis (the implanted device). This also allows for a reduction of energy consumption by delivering only stimulation that is suitable for the given condition. This detection is also used to control the operation of certain cardiac rate control algorithms such as the so-called fallback and smoothing algorithms. In addition, the detection of the spontaneous ventricular rate, in particular the analysis of its stability, are important parameters in certain implantable defibrillators for the release of a shock therapy.

The checking of the effectiveness of the stimulation is an important feature to maintain the implanted device in its optimal operating range. This is done by performing what is called a "capture test" that measures an "evoked potential", i.e., the potential of the depolarization wave induced by a stimulation of the cavity being monitored, using an intracardiac lead (also called a probe) having an electrode in contact with the myocardium. The evoked potential signal maybe distorted, however, by disturbances that are related to the behavior of the sensing circuit amplifiers just after stimulation. A first type of disturbance comes from the discharge of the electric charges at the electrode/myocardium interface. To eliminate the effects of this disturbance, one envisages a period known as a "refractory period" during which a disconnection (also referred to as a "blanking") of the sensing circuits is operated, typically for a length of time of about 13 ms. By comparison, a stimulation pulse has a maximum duration of about 1 ms. This blanking period typically is an "absolute" blanking period in which no signals are detected, and is more typically followed by a period of waiting or "listening" for an evoked response, of a typical duration of about 50 ms. The signal delivered by the sensing circuits during this listening period is however disturbed by another factor, specific to the sensing detection amplifier, because of a phenomenon of "rebound" of the amplifier at the time when it is reconnected to the sensing electrode at the conclusion of the blanking period.

This potential specific to the amplifier is hereafter referred to as a "response potential." The signal delivered by the sensing circuit amplifier will thus include, if it is present, the evoked potential resulting from the depolarization of the cavity, on which a specific response potential from the amplifier will be superimposed. The presence and the level of the amplifier response potential will be primarily independent of the presence or the absence of a depolarization; it is thus likely to disturb the capture test, particularly when the depolarization wave has a low amplitude, as is the case, for example, with an atrial depolarization wave because of the small muscular mass of the atrium.

OBJECTS AND SUMMARY OF THE INVENTION

It is an object of the present invention to propose a device able to determine this response potential specific to a sensing amplifier, and to minimize the masking effect of the response potential in order to increase the quality of the capture test.

One advantageous application—and it should be understood that the invention is not limited to this particular application—of the present invention is in the context of a "cycle to cycle" capture test, used in certain recent active implantable medical devices where one seeks to reduce the stimulation voltage to a level close that is to the capture threshold. The capture threshold is the voltage level below which there is no capture, i.e., a stimulation pulse will not cause a stimulated heartbeat. Such a reduction of voltage has the advantage of reducing the energy of the applied stimulation, and thus the corresponding energy consumption of the device, increasing thus correlatively the lifespan of the implant. The counterpart to using a voltage level that is close to the capture threshold is the need for frequently checking, typically at each cardiac cycle, rather than at periodic intervals (for example, every six hours), whether the stimulation was effective, so as to readjust the stimulation voltage and/or apply a voltage corresponding to a safe amplitude (i.e., one that will produce a stimulation).

The present invention thus proposes an improvement of the known devices including a stimulation means, able to deliver to at least one cardiac cavity pulses of predetermined voltage levels and widths, and means for sensing the cardiac activity, comprising at least one amplifier of the signals sensed by an intracardiac electrode, delivering at its output a value of a measured potential consecutive to the application of a stimulation pulse by the stimulating means. Such stimulating and sensing means are respectively known in the art and can be any of a variety of known stimulation circuits and sensing circuits.

According to the invention, the device further includes means for determining a response potential of the sensing circuit amplifier, independently of the presence or absence of a myocardial depolarization.

Advantageously, the device further includes a compensating means able to extract, from the value of the measured potential consecutive to the application of a stimulation pulse the specific value of the amplifier response potential corresponding to the width and the level of voltage of the aforementioned stimulation pulse. By this technique the device obtains the sensed depolarization potential more accurately, reflecting the evoked potential for use in, e.g., a capture test. In this regard, after delivery of a stimulation pulse by the stimulating means, in performing the capture test, the potential value delivered at the output of the compensating means is compared to a predetermined threshold and, if the value is higher than the threshold, it is determined that an evoked potential resulting from a myocardial depolarization and capture are present.

In a preferred embodiment, the means for determining the specific response potential from the amplifier includes a means for applying at least two stimulation pulses, each one able to cause a depolarization and for which the voltage levels and/or the pulse widths are different, and means, starting from the respective sensed measured potentials corresponding to these two pulses, for determining a linear relation, including a constant and a proportionality factor, relating the level of the measured potential to the product of the pulse width by the pulse voltage level.

BRIEF DESCRIPTION OF THE DRAWING

Other features, characteristics and advantages of the present invention will appear to a person of ordinary skill in the art in view of the following detailed description, made with reference to the drawing annexed, which schematically illustrates the variation over time of the amplitude of the signal delivered by the amplifier of the sensing circuit of the cardiac activity.

DETAILED DESCRIPTION OF THE INVENTION

As indicated above, an object of the present invention is the determination of a response potential specific to the amplifiers of the circuits used for sensing the cardiac activity at the time of the period of measurement following immediately the blanking period, after the delivery of the stimulation pulse.

The potential V delivered at the sensing circuit amplifier output presents the characteristic form illustrated in FIG. 1, and gives the evolution of the voltage signal V according to time T (for the convenience of the illustration, the real time scale is not respected in FIG. 1).

First of all, the device delivers an stimulation pulse I having an amplitude (voltage level) Vs and a width (pulse duration) Ls. These two parameters, Vs and Ls, can both vary in broad proportions, according to the control parameters of the implanted device, in this exemplary embodiment, a pacemaker. The amplitude Vs typically lies between 1.5 and 7.5 V, adjustable by step increments of 0.5 V, and the pulse width Ls typically lies between 0.12 and 0.98 ms, adjustable by 0.12 ms step increments. The stimulation energy is proportional to the width Ls and to the square of the pulse amplitude Vs.

After each application of a pulse, an absolute blanking period of typical duration T1=13 ms is envisaged, followed by a listening period of measurement, typically of a duration T2−T1=50 ms, during which the evoked response is awaited.

For these periods, the voltage delivered at the sensing circuit amplifier output evolves in the illustrated way, with a rebound of voltage due in particular to the discharge of the parasitic capacities of the amplifier at the time when the amplifier is re-connected at the end of the blanking period. More precisely, the device determines the excursion of voltage Pmeasured, which is considered as the starting value from which the calculations described thereafter will be carried out.

The device evaluates an amplitude value thus including the depolarization potential (if it is present), on which a specific response potential from the amplifier is superimposed; this response potential is of course a parasitic potential that may mask the depolarization potential that is possibly present, and it will be thus necessary to take account of it to evaluate the presence (or not) of the depolarization potential in the total sensed signal. The difficulty in operating this discrimination is increased by the fact that the specific response potential from the amplifier is not a constant value, but varies according to the stimulation pulse previously applied.

The present invention thus rests on four basic assumptions:

1. The signal delivered by the amplifier is the sum of the depolarization potential and the amplifier response potential;
2. The amplifier response potential is proportional to the stimulation voltage Vs;
3. The amplifier response potential is proportional to the stimulation pulse width Ls; and
4. Because the stimulation pulse energy is sufficient to depolarize the myocardium, the evoked potential is independent of the stimulation energy: in other words, according to whether one is located above or below the capture threshold, the evoked potential is either null (zero), or of an appreciably constant value for a given cavity; the depolarization potential thus does not vary in a linear manner with the stimulation energy, unlike the amplifier response potential.

If one indicates the signal Pmeasured measured at the amplifier output by the amplifier, the depolarization potential Pstim, and the response potential specific to the amplifier Pampli, they form the following relations:

Pmeasured=Pstim+Pampli, and

Pampli=$K(Vs)(Ls)$

On these bases, it is then possible to define a technique for the measurement of the depolarization potential Pstim, independently of the amplifier response potential Pampli, in order to control the implant according to the presence or the absence of a capture.

To this end, the device is controlled so as to apply two stimulation pulses presenting different widths and/or voltage levels, but in a way that one is certain that these pulses will all be captured, i.e., will cause with certainty a cardiac depolarization. In other words, one defines two couples of values {Vi, Li} and {Vj, Lj} ensuring the capture of the myocardium. For each one of these pulses one measures the total potential Pmeasure delivered by the amplifier, that is to say:

Pmeasured($i$)=Pstim+Pampli($i$), and

Pmeasured($j$)=Pstim+Pampli(j).

By substituting the above relation for Pampli, these equations can be rewritten as follows:

Pmeasured($i$)=Pstim+$K(Vi)(Li)$, and

Pmeasured($j$)=Pstim+$K(Vj)(Lj)$.

One thus constitutes a system of two equations with two unknown factors, Pstim and K, which makes it possible to solve for the two unknowns, K and Pstim, by calculation in a known manner.

Once the proportionality factor K is determined for the sensing amplifier, it is possible, for any later stimulation, to eliminate from the delivered signal Pmeasured the specific response potential Pampli of the amplifier, and thus to establish with an excellent degree of certainty a compensated value Pstim and the presence or the absence of the depolarization potential consecutive to the stimulation pulse. In other words, by extracting the specific response potential of the sensing amplifier, the compensated potential Pstim is obtained corresponding to the depolorization potential at the sensing amplifier output. This compensated potential Pstim then can be used in a capture test by comparison to a predetermined threshold, to determine whether an evoked potential of a capture has occurred.

The relations binding the depolarization evoked potential and the measured potential having been thus established in an unequivocal way, it is possible to evaluate by extrapolation the response which one should obtain for other stimulation voltage levels, pulse widths, and energies, and thus to control detection of the presence of Pstim, therefore to determine more reliably whether there was capture.

It should be understood that the present invention is preferably implemented in a microprocessor controlled active implantable medical device in which the acquired potentials can be digitized and processed by suitable software instructions that implement the functions described above. Moreover, suitable software instructions to produce the desired operations and control signals for the circuit structures disclosed herein in a microprocessor controlled device are deemed to be well within the ability of a person of ordinary skill in the art. Such software controlled devices include, for example, and without limitation, the Chorus, Talent, Chorum, Alto and Defender brand implantable devices for cardiac rhythm management, all available from ELA Medical, Montrouge, France. It also is believed that suitable software also can be downloaded into already installed devices to implement the present invention in those devices that can receive and execute new software instructions.

One skilled in the art will appreciate that the present invention can be practiced by other than the described embodiment, which is presented for the purposes of illustration and not of limitation. Indeed, the circuit parameters and values for voltages and widths should be considered merely as illustrative of useful values, but should not be viewed as limiting as these values may be changed without departing from the present invention

I claim:

1. An active implantable medical device, including:
stimulation means for delivering in at least one cardiac cavity stimulation pulses having a predetermined voltage level and a predetermined pulse width, and
means for sensing cardiac activity including an evoked potential corresponding to a myocardial depolarization, said sensing means comprising at least one amplifier of signals sensed by an intracardiac electrode, said sensing means having an output and delivering at its output a measured potential value consecutive to a delivered stimulation pulse, wherein the improvement comprises:
means for determining a specific response potential of the sensing means amplifier independently of a presence or absence of a myocardial depolarization, in which the determining means further comprises:
means for applying at least two stimulation pulses in two different cycles able to cause a myocardial depolarization, the stimulation voltage level or pulse width of one of said two stimulation pulses being different from the stimulation pulse voltage level or pulse width of the other of said two stimulation pulses, and
means for determining, in response to the respective measured potentials sensed in responds to said at least two stimulation pulses in two different cardiac cycles, a constant and a proportionality factor of a linear relation relating the measured potential to the product of the stimulation pulse width by the stimulation pulse voltage level.

2. The device of claim 1, further comprising compensating means for extracting from the measured potential value the value of said specific response potential from the amplifier corresponding to the predetermined pulse width and voltage level, and producing a compensated potential corresponding to the detected depolorization potential.

3. The device of claim 2, further comprising means for performing a capture test in response to a delivered stimulation pulse, including:
means for comparing the compensated potential to a predetermined threshold; and
means for deciding the presence of an evoked potential resulting from a myocardial depolarization if the compensated potential is higher than the predetermined threshold.

* * * * *